United States Patent
Hajnsek

(10) Patent No.: US 9,993,187 B2
(45) Date of Patent: Jun. 12, 2018

(54) ELECTROCHEMICAL AND LUMINESCENT SENSOR STRUCTURES INTEGRATED ON COMMON SUBSTRATE

(71) Applicant: Joanneum Research Forschungsgesellschaft mbH, Graz (AT)

(72) Inventor: Martin Hajnsek, Graz (AT)

(73) Assignee: JOANNEUM RESEARCH FORSCHUNGSGESELLSCHAFT MBH & CO. KG, Graz (AT)

( * ) Notice: Subject to any disclaimer, the term of this patent is extended or adjusted under 35 U.S.C. 154(b) by 634 days.

(21) Appl. No.: 14/603,157

(22) Filed: Jan. 22, 2015

(65) Prior Publication Data

US 2015/0223742 A1    Aug. 13, 2015

(30) Foreign Application Priority Data

Jan. 23, 2014 (GB) .................................. 1401107.6

(51) Int. Cl.

| | |
|---|---|
| *A61B 5/05* | (2006.01) |
| *A61B 5/1486* | (2006.01) |
| *A61B 5/145* | (2006.01) |
| *A61B 5/1459* | (2006.01) |
| *G01N 21/64* | (2006.01) |

(Continued)

(52) U.S. Cl.
CPC ........ *A61B 5/14865* (2013.01); *A61B 5/1459* (2013.01); *A61B 5/1473* (2013.01); *A61B 5/14532* (2013.01); *A61B 5/4839* (2013.01); *A61B 5/6852* (2013.01); *G01N 21/64* (2013.01); *G01N 21/6428* (2013.01); *G01N 21/6486* (2013.01); *A61B 5/1455* (2013.01); *A61B 5/1468* (2013.01); *A61B 5/1486* (2013.01); *A61B 5/14556* (2013.01); *A61B 5/14735* (2013.01); *C12Q 1/006* (2013.01)

(58) Field of Classification Search
CPC . A61B 5/14865; A61B 5/4839; A61B 5/6852; A61B 5/14735; A61B 5/1468; A61B 5/1486; G01N 21/6486; G01N 21/64; G01N 21/6428; C12Q 1/006
See application file for complete search history.

(56) References Cited

U.S. PATENT DOCUMENTS

| | | |
|---|---|---|
| 5,299,571 A | 4/1994 | Mastrototaro |
| 2001/0026775 A1 | 10/2001 | Biebernik et al. |

(Continued)

FOREIGN PATENT DOCUMENTS

| | | |
|---|---|---|
| EP | 1672356 A1 | 4/2012 |
| WO | 2004060446 A2 | 7/2004 |

(Continued)

*Primary Examiner* — Navin Natnithithadha
*Assistant Examiner* — Andrey Shostak
(74) *Attorney, Agent, or Firm* — Robert A. Blaha; Smith Tempel Blaha LLC

(57) ABSTRACT

A sensor arrangement for detecting information indicative of a physiological substance in a body material of a physiological subject, wherein the sensor arrangement comprises a substrate, a first sensor structure connected to the substrate and being configured for sensing the physiological substance electrochemically, and a second sensor structure connected to the substrate and being configured for sensing the physiological substance by a luminescence detection.

16 Claims, 3 Drawing Sheets

(51) Int. Cl.
*A61B 5/00* (2006.01)
*A61B 5/1468* (2006.01)
*A61B 5/1455* (2006.01)
*A61B 5/1473* (2006.01)
*C12Q 1/00* (2006.01)

(56) References Cited

U.S. PATENT DOCUMENTS

| | | |
|---|---|---|
| 2004/0180391 A1 | 9/2004 | Gratzl et al. |
| 2006/0121547 A1* | 6/2006 | McIntire ............... C12Q 1/002 435/14 |
| 2009/0005724 A1* | 1/2009 | Regittnig ........... A61B 5/14503 604/21 |
| 2009/0240121 A1* | 9/2009 | Bickoff ............. A61B 5/14532 600/309 |
| 2009/0242425 A1* | 10/2009 | Kamath ............. A61B 5/14865 205/777.5 |
| 2012/0037513 A1 | 2/2012 | Lindemann |
| 2013/0060105 A1* | 3/2013 | Shah .................. A61B 5/6849 600/316 |
| 2014/0005505 A1 | 1/2014 | Peyser et al. |

FOREIGN PATENT DOCUMENTS

| | | | |
|---|---|---|---|
| WO | 2010118537 A1 | 10/2010 | |
| WO | 2010142590 A1 | 12/2010 | |
| WO | WO 2010142590 A1 | 12/2010 | |
| WO | WO 2013106155 A1 * | 7/2013 | ......... A61B 5/14532 |

* cited by examiner

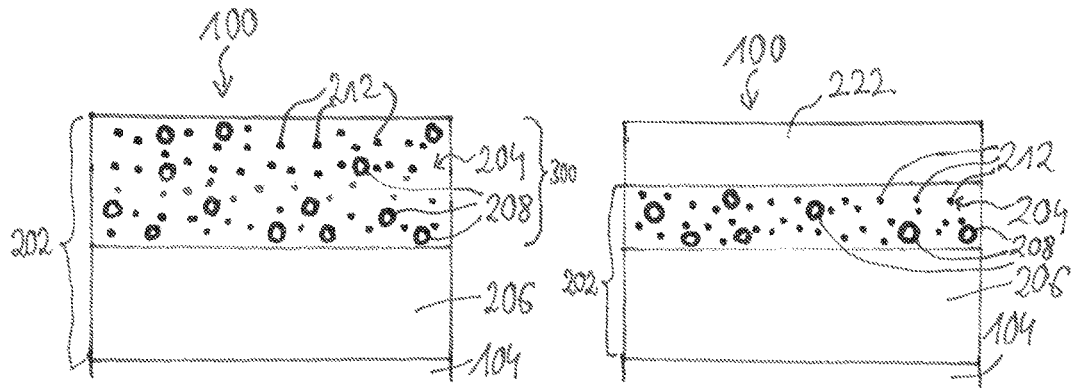
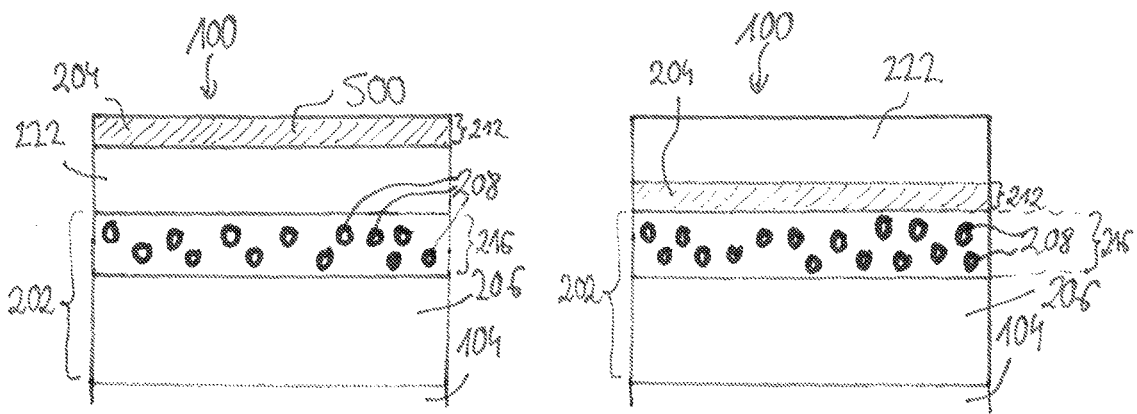
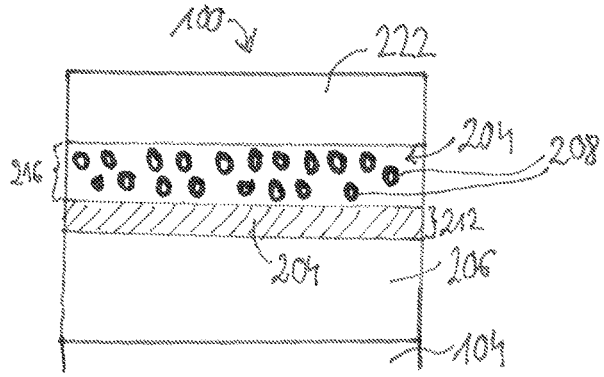

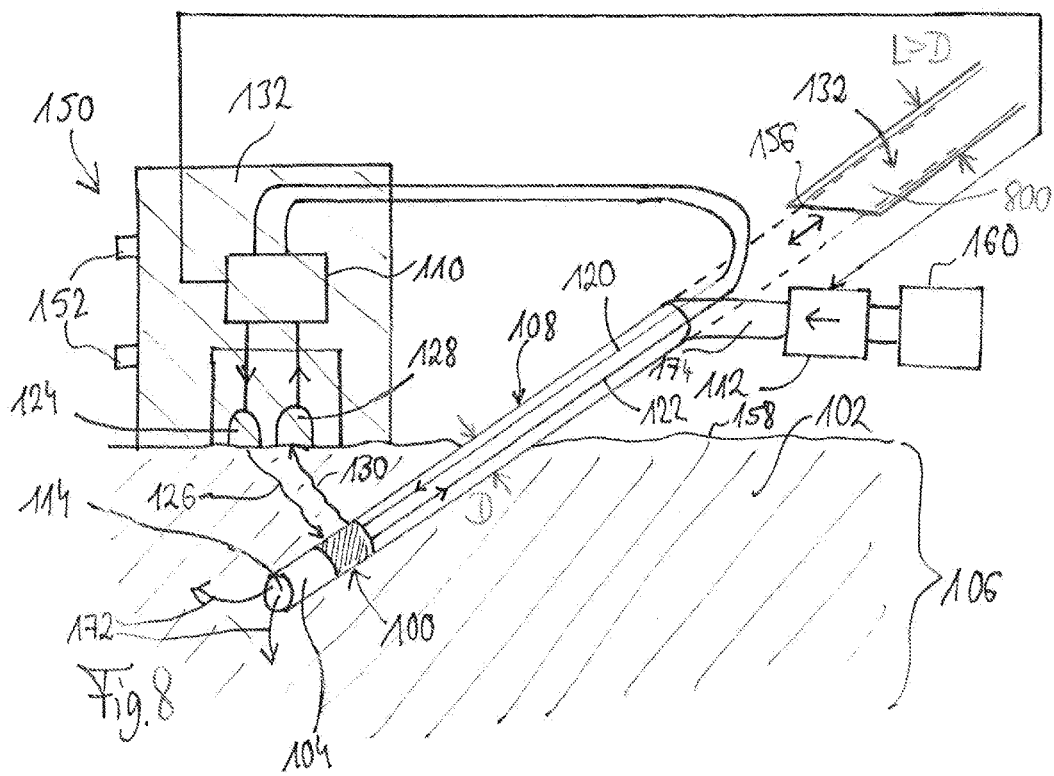

ELECTROCHEMICAL AND LUMINESCENT SENSOR STRUCTURES INTEGRATED ON COMMON SUBSTRATE

CROSS-REFERENCE TO RELATED APPLICATION

This application claims priority to GB 1401107.6 filed 23 Jan. 2014, the entire content of which is hereby incorporated by reference.

TECHNICAL FIELD

The invention relates to a sensor arrangement for detecting a physiological substance in a body material.

Moreover, the invention relates to a monitoring system for monitoring a physiological substance in a physiological subject.

Beyond this, the invention relates to a method of detecting a physiological substance in a body material.

Furthermore, the invention relates to a method of manufacturing a sensor arrangement for detecting a physiological substance in a body material.

BACKGROUND

For patients who have to permanently monitor the concentration of a specific analyte in the body and provide to the body medicaments for adapting this analyte concentration to physiological values, a considerable effort arises. So, for example patients with diabetes have to measure multiple times a day the blood glucose values which are used as a basis for a therapy decision. In doing so, the skin is perforated for example with a lancet and the thereby emerging blood is applied on a measuring strip as part of a measuring system. After availability of the measurement value the insulin dose is calculated wherein the insulin is injected into the subcutaneous tissue by means of a needle. This measurement/injection cycle is associated with two skin penetrations causing pain. Further, the insulin is administered in a "non-physiological" dosage. For optimizing the uniform dosage, insulin pumps have been developed which continuously deliver the insulin through an implantable catheter. Besides the advantage of the continuous delivery of the insulin, the pump catheter may reside in the tissue for a longer time, whereby a multiple piercing is omitted and the inconveniences associated therewith can be avoided.

WO 2010/142590 discloses a device for the transcutaneous, in vivo measurement of the concentration of at least one analyte in a living organism, comprising a carrier which can be introduced into the organism, and a luminescence indicator, which is immobilized on the carrier and which reacts to a change in the concentration of the analyte to be measured with a change in at least one optical property, wherein the luminescence indicator is transcutaneously connected to a source for providing the excitation radiation and a detector for detecting the measuring radiation. The luminescence indicator is immobilized on the outer circumference of a catheter, which is used to dispense a fluid medium, for example a medication, into the organism or to drain a body fluid.

Hence, the system according to WO 2010/142590 provides a compact device for measuring the glucose level. However, in the unlikely event of a failure of the luminescence indicator, a measurement of the glucose level is no longer reliably possible.

US 2013/0060105 discloses a continuous glucose monitoring system which may include a hand-held monitor, a transmitter, an insulin pump, and an orthogonally redundant glucose sensor, which may comprise an optical glucose sensor and a non-optical glucose sensor. The former may be a fiber optical sensor, including a competitive glucose binding affinity assay with a glucose analog and a luminophore-labeled glucose receptor, which is interrogated by an optical interrogating system, for instance a stacked planar integrated optical system. The non-optical sensor may be an electrochemical sensor having a plurality of electrodes distributed along the length thereof. Proximal portions of the optical and electrochemical sensors may be housed inside the transmitter and operationally coupled with instrumentation for, for instance, receiving signals from the sensors, converting to respective glucose values, and communicating the glucose values. The sensors' proximal portions may be inserted into a user's body via a single delivery needle and may be co-located inside the user's body.

The system according to US 2013/0060105 has the advantage that the glucose level measurement is still possible when one of the two orthogonal redundant glucose sensor fails. It is however a shortcoming of such a system that the resulting devices require a lot of space.

SUMMARY

It is an object of the invention to provide a failure robust and accurate sensor arrangement for detecting a physiological substance in a body material which can be manufactured in a compact way.

In order to achieve the object defined above, a sensor arrangement for detecting a physiological substance in a body material, a monitoring system for monitoring a physiological substance in a physiological subject, a method of detecting a physiological substance in a body material, and a method of manufacturing a sensor arrangement for detecting a physiological substance in a body material according to the independent claims are provided.

According to an exemplary embodiment of the invention, a sensor arrangement for detecting information indicative of a physiological substance (for instance for detecting a concentration of the physiological substance) in a body material (such as subcutaneous tissue, interstitial fluid and/or blood) of a physiological subject is provided, wherein the sensor arrangement comprises a substrate, a first sensor structure connected to (for instance integrally formed with or formed on and/or in and/or above) the substrate and being configured for (qualitatively or quantitatively) sensing the physiological substance electrochemically (wherein electrochemical may denote any interaction or interconversion of electric and chemical phenomena), and a second sensor structure connected to the substrate (for instance integrally formed with or formed on and/or in and/or above the substrate and/or the first sensor structure) and being configured for sensing the physiological substance (qualitatively or quantitatively) by a luminescence detection (wherein luminescence particularly covers fluorescence and phosphorescence; luminescence can be denoted as the emission of electromagnetic radiation by a substance resulting from cold body radiation, rather than by heat, and can be caused by chemical reactions).

According to another exemplary embodiment of the invention, a monitoring system for monitoring a physiological substance in a body material of a physiological subject is provided, wherein the monitoring system comprises a catheter (which may comprise the above mentioned substrate as an integral part of the catheter, or alternatively the substrate may be provided as a separate member attached to the catheter) being implantable (partly or completely) in the physiological subject, a sensor arrangement having the above mentioned features and being integrated with the catheter so that the first sensor structure and the second sensor structure are brought in interaction with the body material comprising the physiological substance in the physiological subject when the catheter is implanted in the physiological subject, an evaluation unit configured for evaluating a first sensor signal and a second sensor signal of the sensor arrangement in common (i.e. using both the first sensor signal and the second sensor signal for deriving the information indicative of the physiological substance and being output as an overall result of the measurement), wherein the first sensor signal is detected as an electrochemical response of the first sensor structure upon interaction of the physiological substance with the first sensor structure, and the second sensor signal is detected as a response (such as a change) of luminescence properties of the second sensor structure upon interaction with the physiological substance.

According to still another exemplary embodiment of the invention, a method of detecting a physiological substance in a body material of a physiological subject is provided, wherein the method comprises bringing a sensor arrangement in interaction with the body material comprising the physiological substance, wherein the sensor arrangement has a substrate connected with a first sensor structure configured for sensing the physiological substance electrochemically and connected with a second sensor structure configured for sensing the physiological substance by a luminescence detection, detecting a first sensor signal indicative of the physiological substance based on an electrochemical response of the first sensor structure upon interaction with the physiological substance, detecting a second sensor signal indicative of the physiological substance based on luminescence properties of the second sensor structure upon interaction with the physiological substance, and evaluating the first sensor signal and the second sensor signal in common.

According to still another exemplary embodiment of the invention, a method of manufacturing a sensor arrangement for detecting information indicative of a physiological substance in a body material is provided, wherein the method comprises connecting a first sensor structure to (particularly directly onto) a substrate and configuring the first sensor structure for sensing the physiological substance electrochemically, and connecting a second sensor structure to the substrate (particularly connecting the second sensor structure directly onto the first sensor structure which may, in turn, be connected directly onto the substrate) and configuring the second sensor structure for sensing the physiological substance by a luminescence-based detection.

The term "catheter" may particularly denote a tube (or any differently shaped geometrical structure) that can be inserted into a physiological body, wherein upon inserting the catheter into the physiological body, the catheter may generate itself a cavity in which the catheter is accommodated. A catheter may be a flexible tube. In other embodiments, a catheter may be a stiff tube. Its diameter may vary particularly between 0.2 mm and 10 mm.

The term "physiological subject" or biological object may particularly denote any human being, any animal, and any plant (any organism).

The term "physiological substance" may particularly denote any substance which occurs naturally within a physiological subject and is therefore related to the physiology of a living organism, for instance the metabolism, etc. Such a physiological substance may include a biochemically active molecule (such as glucose), a hormone, a protein, etc.

The term "physiologically active substance" may particularly denote any substance which may have an effect on the physiology of the living organism, for instance a medication, a drug, etc.

A gist of an exemplary embodiment is that an orthogonally redundant detection system for detecting a physiological substance in a body material is provided in which an electrochemically-based sensor and a luminescence-based sensor are integrated together within a single common substrate (for instance an integral layer stack in which both an electrochemical sensor structure as well as a luminescent sensor structure is embedded) so as to obtain a high compactness as well as a high reliability of the measurement at the same time. Layers of such a layer stack may have a thickness in one dimension which is significantly smaller, particularly at least five times smaller, than extensions of the layer in other dimensions. When one sensor fails in an exceptional case, the other one is still able to provide the desired information. When both sensors work, the orthogonal redundancy provides for an improved high accuracy of the measurement result. The integral formation of both sensor structures on and/or in and/or above the same substrate results in a small dimensioned sensor arrangement and in the occurrence of the sensor events related to both the electrochemically-based measurement as well as the luminescence-based measurement basically at the same location and therefore based on the same physical sample of physiological substance. In other words, the first sensor structure and the second sensor structure can be arranged in such a close spatial relationship that one and the same educts and/or products of one and the same biochemical reaction have simultaneously an impact on both the luminescence-based measurement and to the electrochemical measurement. Thus, exemplary embodiments allow to efficiently suppress artefacts which conventionally result from the use of different volumes of sample material for different measurements of the physiological substance at different locations. Thus, the comparability of the measurements as well as the result of the common evaluation can be significantly improved.

More specifically, an exemplary embodiment of the invention allows the manufacture of a sensor arrangement providing orthogonal redundancy by the combination of two sensing technologies on one and the same sensor arrangement: an electrochemical sensor for detecting a physiological substance such as glucose, which electrochemical sensor benefits from a cover layer which can be formed as a diffusion barrier for the physiological substance and electrically detects the glucose level by an electrode buried beneath the cover layer; and a luminescence-based sensor, such as a fluorescence-based glucose sensor, which can be realized by implementing a luminescence substance, such as a fluorescent dye, in the cover layer. Consequently, the conversion of the same physiological substance (such as glucose) can be read out electrochemically at the electrode as well as optically by inspecting the luminescence substance of the cover layer. By such embodiments, it is possible to read out one and the same sensor optically as well as electrochemically. The area consumption of such a sensor arrangement is very small (for instance can be reduced in comparison with two separate sensors by a factor of two), while making benefit of the advantages of an orthogonally redundant measurement.

In the following, further exemplary embodiments of the sensor arrangement, the monitoring system, the method of detecting a physiological substance in a body material, and the method of manufacturing a sensor arrangement will be explained.

In an embodiment, both the first sensor structure and the second sensor structure are configured for detecting glucose as the physiological substance. Such a glucose monitoring may be performed in a body fluid (such as blood or interstitial fluid), in solid body material (such as subcutaneous adipose tissue), etc., as the body material. For example, a chemical reaction used as a basis for the electrochemical and luminescence-based detection is:

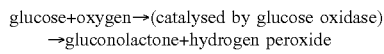

→gluconolactone+hydrogen peroxide

The glucose oxidase enzyme (GOx) is hence an oxidoreductase that catalyses the oxidation of glucose to hydrogen peroxide and D-glucono-δ-lactone.

The electrochemical detection of glucose as physiological substance can be performed by measuring a change of the electric properties (such as a change in the current flow or a voltage) of an electrode of the first sensor structure as a result of the oxidation of the hydrogen peroxide generated by the above reaction. For instance, the current flow at the electrodes is considered to be dependent on the concentration of hydrogen peroxide produced by the above reaction.

The luminescence based detection of glucose as physiological substance can be performed by measuring the change of the partial oxygen pressure at the second sensor structure, since the oxygen pressure in the second sensor structure influences the luminescence properties of a luminescent substance in the second sensor structure. For instance, a fluorescent dye as luminescent substance may have optical properties (in terms of absorption of electromagnetic radiation and re-emission of other electromagnetic radiation after the absorption) which depend on the surrounding oxygen concentration. Oxygen, in turn, is consumed by the above chemical reaction in an amount which corresponds to the glucose concentration. Hence, a change of the optical properties at the second sensor structure is a fingerprint of the present glucose level in the body material.

In terms of glucose monitoring, the biocompatibility of the sensor arrangement in the optical measurements path can be further increased, since the electrochemical sensor advantageously promotes a decomposition of hydrogen peroxide generated upon an oxidation reaction of the glucose.

Although glucose monitoring is an important application of a sensor arrangement according to an exemplary embodiment, it should be mentioned that the detection of other physiological substances is possible as well according to other embodiments. For instance, the lactate level in a body material may be measured, wherein a suitable enzyme may be used for catalyzing a corresponding reaction, as known by those skilled in the art.

In an embodiment, the substrate comprises a foil (such as a sheet) and/or a tube (such as a hollow cylindrical structure). Since the first sensor structure and the second sensor structure can be formed by applying (for instance depositing) layers of appropriate material on the substrate, basically any substrate can be used as a support for such layer-based sensor structures. When applying such sensor structure layers directly on a tube, the tube itself can in turn be configured as a catheter for insertion into the physiologic object. When forming the sensor structure on a sheet, this sheet can in turn be attached to a support (such as a tube) for performing the dual measurement on the support. For example, such a support can again be a catheter.

In an embodiment, at least one of the first sensor structure and the second sensor structure is configured as at least one layer formed in and/or on and/or above the substrate. By configuring the sensor arrangement as a layer or a layer sequence on the supporting substrate, a highly compact structure is obtained which is suitable for implantation into the physiological subject. By selecting the order of the application of the layers, it is possible to adapt the sensor arrangement to be particularly sensitive in combination with optionally used further external components, such as an optical emitter and an optical detector and/or an electric emitter and an electric detector.

In an embodiment, the first sensor structure comprises an electrode (for instance made of one or more metals such as gold or platinum, or metal oxides such as iron oxides, ruthenium oxides and manganese oxides) and an enzyme (which may catalyze a chemical reaction involving the physiological substance to be detected, for instance glucose oxidase when sensing glucose as physiological substance) included in an enzyme comprising structure (which may, in turn, comprise a matrix in which the enzyme is embedded). In an embodiment, the electrode may be configured for detecting a product (such as hydrogen peroxide in case of glucose monitoring) of an enzyme-catalyzed chemical reaction between the physiological substance and a further educt substance (which may also be denoted as a reactant or a starting substance, such as oxygen in the case of glucose monitoring). Via such an electrode, an electric signal such as an electric current may be measured when the reaction product is oxidized at the electrode.

In an embodiment, the second sensor structure comprises a luminescent substance (for instance a fluorescent substance such as a porphyrin) having luminescent properties which change upon change of an amount of an educt (such as oxygen in case of glucose monitoring) of a chemical reaction between the physiological substance (such as glucose) and the educt. For example, when oxygen is consumed by a glucose-oxygen reaction, the reduction of the partial pressure of oxygen can be detected, since this will also change the fluorescent properties of a fluorescent agent interacting with oxygen. The reduction of the oxygen pressure due to consumption by a glucose-oxygen reaction allows deriving information concerning the concentration of glucose. Hence, the second sensor structure may be configured for sensing the physiological substance by a fluorescent detection as the luminescence detection.

In an embodiment, the electrode is arranged directly on the substrate, the luminescent substance is arranged in a surface portion of the sensor arrangement in direct contact with the body material, and the enzyme is arranged in an enzyme section (such as an enzyme layer) between the electrode and the luminescent substance. In such an embodiment, the physiological substance may be capable of passing the layer accommodating the luminescent substance in which also a further educt (such as oxygen in the case of glucose monitoring) for a physiological substance-educt reaction is present. In the surface layer, interaction between the luminescent substance and one educt occurs. This can be detected optically by directing electromagnetic radiation onto the surface layer and detecting the luminescent response. Arranging the luminescent substance in the surface layer of the sensor arrangement is therefore advantageous for performing the optical measurement with high accuracy. The physiological substance having passed the surface layer comes in interaction with the enzyme layer beneath where the actual catalyzed physiologic substance-educt reaction occurs. The product of this reaction is therefore already in close spatial relationship with the electrode beneath the enzyme layer so that a highly sensitive electrochemical detection of the product is enabled by performing an electric measurement. The reaction in the enzyme layer consumes one educt (oxygen in the case of glucose monitoring). The change in educt concentration leads to a change of the optical properties of the luminescent substance in the surface layer which can be detected optically by directing electromagnetic radiation onto the surface layer and detecting the luminescent response. Therefore, the described arrangement of the individual components of the sensor structures provides for an extremely compact and accurate orthogonally redundant measurement of the level of the physiological substance, or of other properties thereof.

In an embodiment, the surface portion is permeable (to a full or to a limited extent) for the physiological substance. For instance, the surface portion may be formed as a permeable membrane in which the luminescent substance (such as luminescent particles) are embedded.

In an embodiment, the enzyme comprising structure (such as an enzyme layer below the layer with the luminescent substance) is permeable for the product. When the enzyme section is permeable for the product, the product may diffuse towards the electrode, for instance directly beneath the enzyme comprising structure, for performing the electrochemical detection.

In an embodiment, the surface portion is impermeable for the enzyme. By taking this measure, the enzyme is prevented from diffusing out of the enzyme layer into the body material. At the same time, the surface portion may be permeable for the physiological substance so as to bring the latter in interaction with the enzyme.

In an embodiment, at least a part of the first sensor structure and at least a part of the second sensor structure are integrated into a common physical body (such as a common layer or layer sequence) so that a sensor event detectable by the first sensor structure and a sensor event detectable by the second sensor structure both occur within the common physical body. On the one hand, this has the advantage that the required volume for or space consumption of the sensor arrangement is extremely small, so that it can be conveniently implanted into a physiological subject such as a human patient. On the other hand, however this has the additional advantage that the spatial volume in which the electrochemical detection takes place and the spatial volume in which the optical detection take place, strongly overlap or maybe even identical, so that the sensor results of both complementary measurements are directly comparable and therefore provide meaningful results. Thus, artifacts resulting from the fact that the measurements are performed on different portions of the body material may be suppressed efficiently.

In an embodiment, the first sensor structure, the second sensor structure and the substrate are formed as an integral inseparable structure. Therefore, it is easy for a user to operate the sensor arrangement, since only a single piece is to be handled, such as a catheter with the sensor arrangement thereon.

In an embodiment, the second sensor structure is formed on the first sensor structure so that the latter spaces the substrate with regard to the second sensor structure. In other words, the first sensor structure (such as one or more first sensor layers) may be sandwiched between the substrate and the second sensor structure (such as one or more second sensor layers). By this spatial configuration, the optical measurement can be performed in a surface portion of the sensor arrangement which simplifies optical excitation and renders optical detection more accurate. On the other hand, the electrochemical detection can be performed below the surface of the sensor arrangement so that it is not negatively influenced by a direct interaction between the body material and a detection electrode.

In an embodiment, the catheter may be made of a plastic material which may be permeable or impermeable.

In an embodiment, the catheter is a catheter tube, wherein the sensor arrangement is arranged circumferentially at a proximal position (i.e. at or close to an end of the catheter tube facing the, or directed towards the physiological subject) of the catheter tube. Particularly, the sensor arrangement may be provided as an annular structure extending around a perimeter at or next to a proximal end of the catheter tube. It is alternatively also possible that the sensor arrangement is provided as a sheet (such as a strip) adhered to or deposited on the catheter. By locating the sensor arrangement at a proximal position of the catheter tube, it is at a position at which the interaction with the body material is not negatively influenced by effects which may occur close to a surface of the physiological subject.

In an embodiment, the monitoring system comprises a supply unit configured for supplying a physiologically active substance (for instance in form of a fluid), particularly a medication such as insulin, to the physiological subject (such as a human or an animal) in a quantity depending on a result of the evaluation unit. In view of the high accuracy of the redundant dual measurement of the level of the physiological substance by the sensor arrangement according to an exemplary embodiment, the result of the measurement is precise enough to base a quantitative supply of a physiologically active substance (for influencing a physiological state of the physiological subject) to the physiological subject (particularly to the body material) in accordance with the measurement results. For example, when the glucose level has been determined electrochemically and optically, an amount of insulin to be supplied to the physiological subject to compensate for an undesired change of the glucose level or deviation of the glucose level from a target value can be calculated based on the measurement results and can be supplied to the physiological subject by the supply unit. The supply unit may comprise a pump being controlled by the evaluation unit. The pump may deliver, under control of the evaluation unit, an amount of physiologically active substance which can be adjusted by adjusting the pumping performance.

In an embodiment, the supply unit is configured for supplying the physiologically active substance to the physiological subject via a permeable section of the catheter. In one embodiment, a through hole is formed in the catheter, for instance at a proximal end of a tubular catheter (for example at a flange face thereof). In another embodiment, the material of the wall of the catheter may be configured, partly or entirely, as a permeable membrane or as a mesh of filaments through which the physiologically active substance may diffuse or may be pressed. It is also possible that the wall of the catheter is at least partially slitted so that the physiologically active substance may be supplied to the body material via one or more slits. Thus, a compact system of monitoring the level of the physiological substance and of delivering a physiologically active substance in an amount corresponding to the result of the monitoring may be provided.

In an embodiment, the monitoring system comprises an electrically conductive signal supply structure (such as a first wiring) configured for transmitting an electric stimulus signal to the first sensor structure, and an electrically conductive detection structure (such as a second wiring) configured for transmitting an electric detection signal to the evaluation unit. The electric detection signal may be generated or modified at the first sensor structure in response to the electric stimulus signal upon interaction of the sensor arrangement with the physiological substance. For instance, an electric voltage may be applied to the electrically conductive signal supply structure and consequently to a measurement electrode of the first sensor structure (particularly may be applied between the electrically conductive signal supply structure and the electrically conductive detection structure), and a resulting current flow may be detected via the electrically conductive detection structure. Such a current is characteristically influenced by the present level of the physiologically active substance when a product of a chemical reaction consuming the physiological substance is oxidized at the electrode inducing an electrical current to the electrode.

In an embodiment, at least one of the electrically conductive signal supply structure and the electrically conductive detection structure is accommodated at least partially on and/or integrated within a wall of the catheter. For example, a corresponding wiring structure may be guided along an interior and/or along an exterior surface of the catheter tube (for example along an axial direction thereof) and/or may be integrated within the wall of such a catheter tube. Such a wiring structure may be adhered to the wall of the catheter or may be sputtered onto a surface of the catheter tube (for instance with a thickness of 10 nm to 100 nm). Optionally, the wiring structure may be electrically insulated.

In an embodiment, the monitoring system comprises an electromagnetic radiation source (such as a light source) configured for transmitting primary electromagnetic radiation to the second sensor structure, and an electromagnetic radiation detector (such as a light detector) configured for detecting secondary electromagnetic radiation generated at the second sensor structure (for instance by fluorescence) in response to the primary electromagnetic radiation upon interaction with the physiological substance, and configured for transmitting a corresponding detection signal to the evaluation unit (which may also be configured as a control unit for controlling operation of the entire monitoring system). Such an electromagnetic radiation source may be a light emitting diode (LED)/photodiode irradiating electromagnetic radiation in an appropriate wavelength range so as to excite fluorescent material of the luminescence agent in the second sensor structure. For instance, such an LED may emit electromagnetic radiation in a range between 600 nm and 800 nm. In response to the absorption of this electromagnetic radiation, the luminescent agent will emit a secondary electromagnetic radiation having a longer wavelength, for instance in a range between above 600 nm and 900 nm. The electromagnetic radiation detector may be configured for detecting electromagnetic radiation in this wavelength range and may for instance be configured as a photodetector/photodiode.

In an embodiment, the monitoring system comprises a support body (such as a plastic plate) to be located outside of the physiological subject and accommodating the electromagnetic radiation source and the electromagnetic radiation detector. Such a support body may be attached to a surface such as the skin of the physiological subject/body material, i.e. in close spatial relationship to the catheter inserted into the physiological subject. Thus, an interaction between the optics within the support body on the one hand and the second sensor structure implanted into the physiological subject is enabled. For instance, the support body may be a lightweight plastic structure. In the support body, further components such as the evaluation unit may be integrated as well.

In an embodiment, the catheter (which may be implanted at least partly in the physiological object) with the sensor arrangement on the one hand and the support body (which may be attached to an outer surface of the physiological object) with the electromagnetic radiation source and the electromagnetic radiation detector on the other hand may be aligned relative to one another in such a way that the primary electromagnetic radiation propagates from the support body through the body material towards the second sensor structure to generate the secondary electromagnetic radiation which, in turn, propagates back from the second sensor structure through the body material towards the support body.

In an embodiment, the monitoring system comprises an insertion needle configured to be selectively insertable into the catheter for inserting, in turn, the catheter into the physiological subject, or to be retractable out of the catheter and out of the physiological subject after the insertion of the catheter into the physiological subject. For implementing the catheter into the physiological subject, the needle within the lumen of the catheter and the catheter itself may both be inserted into the physiological subject, wherein a sharp tip or lancet of the needle may simplify insertion. After the insertion, the needle may be retracted from the catheter so that the catheter alone may remain within the physiological subject so that its lumen may then be used for other purposes, for instance for conducting a physiologically active substance into the body material.

In an alternative embodiment, the monitoring system comprises a hollow insertion needle configured so that the catheter is selectively insertable into the insertion needle for inserting the catheter into the physiological subject and that the insertion needle is retractable relative to the catheter after the insertion of the catheter into the physiological subject. According to this embodiment, the catheter is received in an interior lumen of the needle (which may hence be shaped as a hollow, for example tubular, body) for implanting into the physiological body. After implanting, the needle can then be removed by retracting it relative to the catheter, so that the catheter alone remains in the physiological body. This has the advantage that the needle serves as a as a circumferential protection of the catheter during the implantation.

According to an exemplary embodiment of the invention, a sensor arrangement, a catheter or a monitoring system having the above mentioned features is used for measuring at least one physiological parameter (such as a concentration) of the physiological substance in the physiological subject (or alternatively may be used for in vitro applications). The term "physiological parameter" may particularly denote any parameter which is related to the physiology of a living organism, for instance the metabolism, etc. Such a physiological parameter may be the value of the concentration of the physiological substance.

The aspects defined above and further aspects of the invention are apparent from the examples of embodiment to be described hereinafter and are explained with reference to these examples of embodiment.

The invention will be described in more detail hereinafter with reference to examples of embodiment but to which the invention is not limited.

BRIEF DESCRIPTION OF THE DRAWINGS

FIG. 2, FIG. 3, FIG. 4, FIG. 5, FIG. 6 and FIG. 7 each show a respective cross-sectional view of a sensor arrangement for detecting a physiological substance in a body material according to exemplary embodiments of the invention.

FIG. 8 shows a monitoring system for monitoring a physiological substance in a physiological subject according to another exemplary embodiment of the invention.

DETAILED DESCRIPTION OF EXEMPLARY EMBODIMENTS

Figure 1:
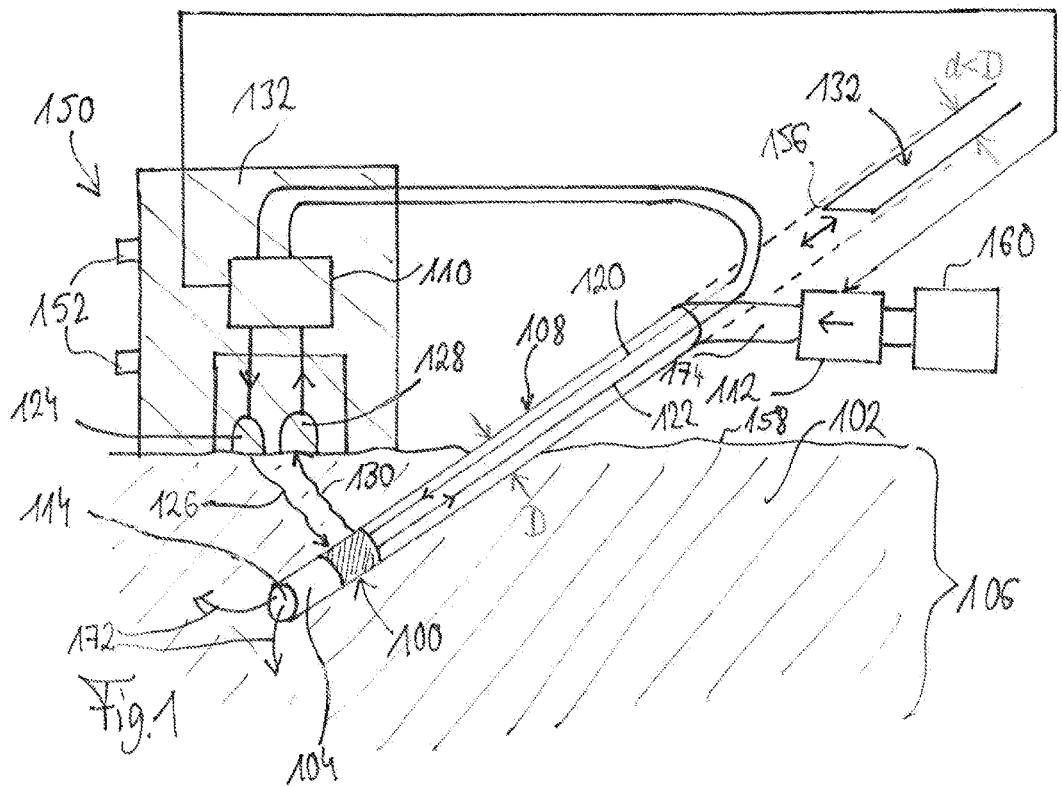
FIG. 1 shows a monitoring system for monitoring a physiological substance in a physiological subject according to an exemplary embodiment of the invention.

The illustration in the drawing is schematically. In different drawings, similar or identical elements are provided with the same reference signs.

FIG. 1 shows a monitoring system 150 for monitoring glucose as a physiological substance in a human as a physiological subject 106 according to an exemplary embodiment of the invention.

The monitoring system 150 comprises a tubular plastic catheter 108 with an impermeable side wall enclosing a lumen 114 for supplying a fluid (see arrows 172) pumped through the lumen 114 to body material 102 via an opening of the catheter 108 at a proximal flange face. A proximal end of the catheter 108 has an open flange face via which a fluid guided through the lumen 114 of the catheter 108 can be transferred into subcutaneous adipose tissue as the body material 102. Hence, the catheter 108 is presently implanted into the body material 102. The body material 102 also comprises a certain concentration of glucose as physiological substance. Via at the open end of the catheter 108, a medication such as insulin can be supplied, as the abovementioned fluid, to the body material 102 in a defined quantity.

A sensor arrangement 100 according to an exemplary embodiment, which will be explained below in further detail, is formed as an integral part of the catheter 108 and is shaped as a ring surrounding an outer circumference surrounding the catheter 108 close to the proximal end thereof. An outer surface of the sensor arrangement 100 is therefore in direct contact and fluid exchange with the body material 102. Via the sensor arrangement 100, the present glucose level in the body material 102 can be sensed accurately by an orthogonally redundant dual measurement. In the present embodiment, the wall of the catheter 108 serves as substrate 104 of the sensor arrangement 100, so that a first sensor structure (compare reference numeral 202 in FIG. 2) and a second sensor structure (compare reference numeral 204 in FIG. 2) can be formed or applied onto the substrate 104.

An evaluation unit 110, which may also be denoted as a control unit and which may be embodied as a microprocessor or a central control unit, CPU, is configured for evaluating in common sensor signals from an electrochemical measurement and from a fluorescence measurement performed by the sensor arrangement 100. Hence, the different individual measurements of an orthogonally redundant dual measurement architecture are both considered (for instance are averaged, compared, etc.) to increase the accuracy of an overall sensor result of the monitoring system 150. The evaluation unit 110 uses the result of the determination of the glucose level in the body material 102 to determine which amount of insulin should be delivered to the body material 102 so as to adjust the glucose level to assume a target value. The evaluation unit 110 then sends a control signal to a fluid pump 112 to supply a predefined amount of insulin from an insulin reservoir 160 to the lumen 114 of the catheter 108 and from there into the body material 102. In view of the high accuracy of the complementary redundant measurement of the glucose level by the sensor arrangement 100, the result of the glucose level determination can be taken as a basis for the calculation of an appropriate insulin supply level.

Figure 2:
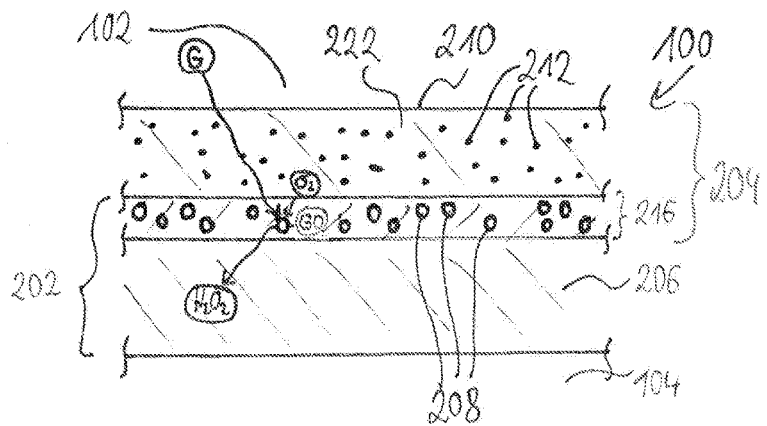

FIG. 2 shows an enlarged cross-sectional view of the sensor arrangement 100 of the monitoring system 150 according to FIG. 1. The sensor arrangement 100 for detecting the glucose level in the body material 102 comprises, as substrate 104 for the below described sensor structures, an annular section of the catheter 108. Alternatively, it is possible to provide a separate tubular or sheet-like substrate 104 to be connected to the catheter 108 by sliding, adhering, etc., as a basis for the deposition or formation of the sensor structures, as described below.

As can be taken from FIG. 2, a first sensor structure 202 being configured for sensing the physiological substance electrochemically is formed and located directly on the substrate 104. On top of the first sensor structure 202, therefore indirectly connected to but also integrally formed with the substrate 104, there is provided a second sensor structure 204 being configured for sensing the physiological substance by a fluorescence based detection. In the shown embodiment, both the first sensor structure 202 as well as the second sensor structure 204 are provided as layer(s) or layer sequence on the substrate 104, thereby forming an integral layer stack. Consequently, the sensor arrangement 100 can be formed in a compact way.

The first sensor structure 202 comprises an electrode 206 which can be made of gold and which is deposited directly on the substrate 104. The electrode 206 can be formed on the plastic substrate 104 by sputtering. It may have a thickness of for instance 50 nm. An enzyme layer 216 comprising an enzyme 208, in the present embodiment comprising or consisting of glucose oxidase, is deposited on the electrode 206. The electrode 206 in combination with the enzyme layer 216 form the first sensor structure 202.

A fluorescent dye 212, for instance benzoporphyrin, is embedded in a permeable membrane 222 to thereby form the second sensor structure 204. The permeable membrane 222 has the function to protect the enzyme 208 particles in the enzyme layer 216 and to limit or control the access of glucose into the sensor arrangement 100. An upper surface of the second sensor structure 204 forms an outer surface 210 of the sensor arrangement 100, i.e. being exposed to the body material 102. In one embodiment, the fluorescent dye 212 may be dissolved in material (such as a precursor) which later forms the permeable membrane 222 by curing or hardening. Alternatively, it is possible to disperse particles of the fluorescent dye 212 into a precursor of the permeable membrane 222. This mixture may then be applied to the first sensor structure 202 by spray coating, dip coating, dispensing, etc. The material of the permeable membrane 222 may be a hydrogel and/or a polymer, both dissolved in an appropriate solvent. The solvent may then be evaporated so that the permeable membrane 222 with the embedded fluorescent dye 212 remains on top of the first sensor structure 202 to thereby constitute the second sensor structure 204.

By means of the described configuration of the sensor arrangement 100 it is possible to perform two measurements of the glucose level within the body material 102, which measurements are based on different detection principles and therefore provide independent information but are nevertheless performed on one and the same fluidic sample, i.e. a part of the body material 102 diffusing into and through the permeable membrane 222, to thereby interact with the first sensor structure 202 and the second sensor structure 204.

As visually indicated in FIG. 2, the electrochemical first sensor structure 202 is constituted by the electrode 206 and the enzyme comprising layer 216. As visually indicated in FIG. 2 as well, the optochemical second sensor structure 204 is constituted by the luminescent agent (e.g., fluorescent dye 212) in the permeable membrane 222 and the enzyme comprising layer 216.

The chemical reaction used as a basis for the electrochemical detection and for the fluorescence-based detection is:

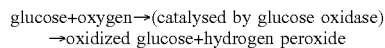

glucose+oxygen→(catalysed by glucose oxidase)
→oxidized glucose+hydrogen peroxide As indicated schematically in FIG. 2, glucose ("G") as the physiological substance to be detected diffuses from the body material 102 through the permeable membrane 222 of the sensor arrangement 100 into the top layer of the first sensor structure 202, i.e. the enzyme comprising layer 216. In the enzyme comprising layer 216, the mentioned chemical reaction takes place in a considerable amount thanks to the catalysing effect of the glucose oxidase as enzyme 208 being present in the enzyme layer 216. As a result or product of this chemical reaction, hydrogen peroxide ($H_2O_2$) is generated, which has the effect to trigger a pronounced oxidation of a surface portion of the electrode 206. Thus, the value of the ohmic resistance/impedance of electrode 206 is characteristically modified in accordance with the glucose level in the body material 102, since the glucose level has a strong impact on the amount of hydrogen peroxide produced. The corresponding change in the electrical properties of electrode 206 can be detected in terms of the above-mentioned electrochemical detection.

As can be taken from the above equation, the mentioned chemical reaction also consumes oxygen ("$O_2$") and produces oxidized glucose ("GO"). The reduction of the oxygen level in the enzyme comprising layer 216 and in its surroundings, therefore also in the layer forming the second sensor structure 204, has an impact on all processes depending on the local partial oxygen pressure. Consequently, also the fluorescent properties of the fluorescent dye 212 in the second sensor structure 204 are influenced by this glucose level-related consumption of oxygen. This can be detected optically, as described below.

Since the first sensor structure 202 and the second sensor structure 204 are integrated into the same physical body, i.e. an annulus surrounding the catheter 108, a sensor event detected by the first sensor structure 202 and a sensor event detected at the second sensor structure 204 both occur within a common, inseparable physical body and in the context of one and the same chemical reaction. Therefore, the measurement results of the first sensor structure 202 and of the second sensor structure 204 are directly comparable, but are nevertheless based on different physical principles and effects, thereby providing complementary or orthogonal information.

Coming back to FIG. 1, the monitoring system 150 furthermore comprises an electrically conductive signal supply structure 120 in form of an electrically conductive wiring which is connected between the electrode 206 and the evaluation unit 110 for transmitting a primary electric signal as a stimulus to the electrode 206 of the first sensor structure 202. An electrically conductive detection structure 122, here embodied also as an electrically conductive wiring, is connected to conduct current from the electrode 206 to the evaluation unit 110. Hence, a secondary electric signal which is generated at the electrode 206 in response to the application of the primary electric signal after the interaction between the physiological substance and the sensor arrangement 100 can be supplied to the evaluation unit 110. Thus, the change of the ohmic resistance/impedance of the electrode 206 being oxidized by the reaction product hydrogen peroxide can be detected by measuring a current flow through the electrode 206 in response to the application of an electric stimulus. The electrically conductive signal supply structure 120 and the electrically conductive detection structure 122 are embodied in FIG. 1 as wiring structures aligned in parallel to one another and to a longitudinal axis of the catheter 108.

Coming to the optical measurement, an electromagnetic radiation source 124 embodied as a photodiode or light emitting diode (LED) is provided for transmitting primary electromagnetic radiation 126 to the second sensor structure 204. When the electromagnetic radiation is in the wavelength range between 600 nm and 800 nm, it excites the fluorescent dye 212 of the second sensor structure 204. In response to this excitation, the fluorescent dye 212 re-emits secondary electromagnetic radiation 130 having a larger wavelength as compared to the primary electromagnetic radiation 126, for instance in a range between above 600 nm and 900 nm. An electromagnetic radiation detector 128, which may be embodied as a photodiode, is arranged for measuring the secondary electromagnetic radiation 130. Since the educt of the above mentioned chemical reduction, i.e. oxygen, is consumed in an amount depending on the glucose level in the body material 102, and since the presence of oxygen has an impact on the characteristics of the fluorescent dye 212, the change of the secondary electromagnetic radiation detected by the electromagnetic detector 128 is a fingerprint of the glucose level. This signal is supplied to the evaluation unit 110 which can correspondingly derive a result of the optic/luminescence measurement.

Both the electromagnetic radiation source 124 and the electromagnetic radiation detector 128 are located within a support body 132 of plastic which is to be located outside of the physiological subject 106, particularly on a skin of the body material 102. The support body 132 may also comprise gripping elements 152 to simplify handling of the support body 132 by a user.

The evaluation unit 110 may then determine an actual value of the glucose level in the body material 102 by combining the measurement results of the electrochemical detection as well as of the optical detection. For instance, an arithmetic average may be calculated. If the deviation of the arithmetic average from the individual measurement results becomes larger than a predefined threshold value, the evaluation unit 110 may output that the measurement result is doubtful. If one of the two measurement values is unreasonably small or large, the evaluation unit 110 may only use the other, reasonable value and may indicate this to a user.

An event triggered by the evaluation unit 110 after having performed the measurement may be to display the result on a display unit (not shown) of the monitoring system 150. Another result may be the output of a warning signal (for instance an optical and/or an acoustical warning signal) indicating that the measurement result is not reliable. Furthermore, the insulin amount to be administered to the body material 102 may be calculated in dependence of the determined glucose level, and the supply unit or pump 112 may be controlled accordingly.

A corresponding control signal may be sent from the evaluation unit 110 to the pump 112. The pump 112 may be fluidically connected to the catheter 108 via a tube or hose 174 (which may for instance have a length between 60 cm and 120 cm). The pump 112 may be carried in a pocket of trousers worn by a user. Alternatively, the pump 112 may also be integrated in the body material 102 (not shown). It is possible that the pump 112 is a patch pump to be adhered on the skin 158 of the physiological subject 106.

FIG. 1 furthermore shows an insertion needle 132, made of a metallic material and having a sharp tip 156. The insertion needle 132 may be inserted into the lumen 114 of the tubular catheter 108 when the latter is to be implanted or inserted into the physiological subject 106. After insertion, the insertion needle 132 is no longer needed and may be retracted from the catheter 108. According to FIG. 1, an outer diameter d of the needle 132 is slightly smaller than an outer diameter D of the catheter 108.

It should be mentioned that the slanted orientation of the catheter 108 with regard to a surface or skin 158 of the physiological subject 106 is only exemplary, and that other orientations are possible as well.

FIG. 3 shows a sensor arrangement 100 for detecting glucose as a physiological substance in subcutaneous adipose tissue as a body material according to an exemplary embodiment of the invention. The embodiment of FIG. 3 differs from the embodiment of FIG. 2 in that the enzyme layer 216 and the permeable membrane/fluorescent dye 212 layer are combined to a single common layer 300.

FIG. 4 shows a sensor arrangement 100 for detecting glucose as a physiological substance in subcutaneous adipose tissue as a body material according to an exemplary embodiment of the invention. The embodiment of FIG. 4 differs from the embodiment of FIG. 3 in that membrane layer 222 is provided separately from and above the second sensor structure 204 having both the enzyme 208 particles and the fluorescent dye 212.

FIG. 5 shows a sensor arrangement 100 for detecting glucose as a physiological substance in subcutaneous adipose tissue as a body material according to an exemplary embodiment of the invention. The embodiment of FIG. 5 differs from the embodiment of FIG. 4 in that the fluorescent dye 212 particles are provided in a separate surface layer 500 above the membrane layer 222 which is, in turn, located above the enzyme layer 216.

FIG. 6 shows a sensor arrangement 100 for detecting glucose as a physiological substance in subcutaneous adipose tissue as a body material according to an exemplary embodiment of the invention. The embodiment of FIG. 6 differs from the embodiment of FIG. 5 in that the two uppermost layers are interchanged.

FIG. 7 shows a sensor arrangement 100 for detecting glucose as a physiological substance in subcutaneous adipose tissue as a body material according to an exemplary embodiment of the invention. The embodiment of FIG. 7 differs from the embodiment of FIG. 6 in that the two layers between the electrode 206 and the membrane layer 222 are interchanged.

FIG. 8 shows a monitoring system 150 for monitoring glucose as a physiological substance in a human as physiological subject 106 according to another exemplary embodiment of the invention.

The embodiment of FIG. 8 differs from the embodiment in FIG. 1 substantially in that the monitoring system 150 comprises a hollow insertion needle 132 configured so that the catheter 108 is selectively insertable into the insertion needle 132 for inserting the catheter 108 into the physiological subject 106 and that the insertion needle 132 is retractable relative to the catheter 108 after the insertion of the catheter 108 into the physiological subject 106. According to FIG. 8, the catheter 108 is received in an interior lumen 800 of the insertion needle 132 during the implanting procedure. After implanting, the insertion needle 132 can then be removed by retracting it relative to the catheter 108 which remains in the body material 102. In other words, an outer diameter L of the insertion needle 132 is here slightly larger than an outer diameter D of the catheter 108.

It should be noted that the term "comprising" does not exclude other elements or steps and the "a" or "an" does not exclude a plurality. Also elements described in association with different embodiments may be combined.

Implementation of the invention is not limited to the preferred embodiments shown in the figures and described above. Instead, a multiplicity of variants are possible which use the solutions shown and the principle according to the invention even in the case of fundamentally different embodiments.

Some particular embodiments may be as follows.

A first embodiment of a sensor arrangement (100) for detecting information indicative of a physiological substance in a body material (102) of a physiological subject (106), includes a substrate (104); a first sensor structure (202) connected to the substrate (104) and being configured for sensing the physiological substance electrochemically; a second sensor structure (204) connected to the substrate (104) and being configured for sensing the physiological substance by a luminescence detection.

The sensor arrangement (100) of the first embodiment, wherein the substrate (104) comprises at least one of a foil and a tube.

The sensor arrangement (100) of one of the preceding embodiments, wherein at least one of the first sensor structure (202) and the second sensor structure (204) is configured as at least one layer formed in and/or on and/or above the substrate (104), wherein particularly the first sensor structure (202) and the second sensor structure (204) together constitute a layer sequence on the substrate (104).

The sensor arrangement (100) of any of the preceding embodiments, wherein the first sensor structure (202) comprises an electrode (206) and an enzyme (208) comprising structure (216), the electrode (206) being configured for electrically detecting a product of an enzyme-catalyzed chemical reaction between the physiological substance and an educt substance.

The sensor arrangement (100) of any of the preceding embodiments, wherein the second sensor structure (204) comprises a luminescent substance (212) having luminescent properties which change upon change of an amount of an educt of a chemical reaction between the physiological substance and the educt.

The sensor arrangement (100) of the two preceding embodiments, wherein the electrode (206) is arranged directly on the substrate (104), the luminescent substance (212) is arranged in a surface portion (210) of the sensor arrangement (100) in direct contact with the body material (102), and the enzyme (208) comprising structure (216) is arranged between the electrode (206) and the luminescent substance (212).

The sensor arrangement (100) of the preceding embodiment, wherein the surface portion (210) is permeable for the physiological substance.

The sensor arrangement (100) of one of the two preceding embodiment, wherein the enzyme (208) comprising structure (216) is permeable for the product.

The sensor arrangement (100) of any of the three preceding embodiments, wherein the surface portion (210) is impermeable for the enzyme (208).

The sensor arrangement (100) of any of the five preceding embodiments, wherein the second sensor structure (204) comprises a permeable membrane in which the luminescent substance (212) is embedded.

The sensor arrangement (100) of any of the preceding embodiments, wherein the second sensor structure (204) is configured for sensing the physiological substance by a phosphorescence detection and/or by a fluorescent detection, as the luminescence detection.

The sensor arrangement (100) of any of the preceding embodiments, wherein at least a part of the first sensor structure (202) and at least a part of the second sensor structure (204) are integrated into a common physical body so that a sensor event detectable by the first sensor structure (202) and a sensor event detectable by the second sensor structure (204) both occur within the common physical body.

The sensor arrangement (100) of any of the preceding embodiments, wherein the first sensor structure (202), the second sensor structure (204) and the substrate (102) are formed as an integral inseparable structure, particularly as a layered stack.

The sensor arrangement (100) of any of the preceding embodiments, wherein the second sensor structure (204) is formed directly on the first sensor structure (202) and the first sensor structure (202) is formed directly on the substrate (204) to thereby space the substrate (104) with regard to the second sensor structure (204).

The sensor arrangement (100) of any of the preceding embodiments, wherein both the first sensor structure (202) and the second sensor structure (204) are configured for detecting glucose as the physiological substance.

A monitoring system (150) for monitoring a physiological substance in a body material (102) of a physiological subject (106), the monitoring system (150) including a catheter (108) being implantable in the physiological subject (106); a sensor arrangement (100) of any of the preceding embodiments integrated with the catheter (108) so that the first sensor structure (202) and the second sensor structure (204) are brought in interaction with the body material (102) comprising the physiological substance in the physiological subject (106) when the catheter (108) is implanted in the physiological subject (106); an evaluation unit (110) configured for evaluating a first sensor signal and a second sensor signal of the sensor arrangement (100) in common, wherein the first sensor signal is detected as an electrochemical response of the first sensor structure (202) upon interaction of the physiological substance with the first sensor structure (202), and the second sensor signal is detected as a response of luminescence properties of the second sensor structure (204) upon interaction with the physiological substance.

The monitoring system (150) of the preceding embodiment, wherein the catheter (108) is a catheter tube, wherein the sensor arrangement (100) is arranged circumferentially at the catheter tube, particularly at a proximal position of the catheter tube.

The monitoring system (150) of the two preceding embodiment, comprising a supply unit (112) configured for supplying a physiologically active substance, particularly a medication such as insulin, to the physiological subject (106) in a quantity depending on a result of the evaluation of the evaluation unit (110).

The monitoring system (150) of the preceding embodiment, wherein the supply unit (112) is configured for supplying the physiologically active substance to the physiological subject (106) via a permeable section (114) of the catheter (108).

The monitoring system (150) of any of the four preceding embodiments, including an electrically conductive signal supply structure (120) configured for transmitting an electric stimulus signal to the first sensor structure (202); and an electrically conductive detection structure (122) configured for transmitting an electric detection signal to the evaluation unit (110), the electric detection signal being generated at the first sensor structure (202) in response to the electric stimulus signal upon interaction of the sensor arrangement (100) with the physiological substance.

The monitoring system (150) of the preceding embodiment, wherein at least one of the electrically conductive signal supply structure (120) and the electrically conductive detection structure (122) is accommodated at least partially on a wall of the catheter (108) and/or integrated within a wall of the catheter (108).

The monitoring system (150) of any of the six preceding embodiments, including an electromagnetic radiation source (124) configured for transmitting primary electromagnetic radiation (126) to the second sensor structure (204); and an electromagnetic radiation detector (128) configured for detecting secondary electromagnetic radiation (113) generated at the second sensor structure (204) in response to the primary electromagnetic radiation (126) upon interaction of the sensor arrangement (100) with the physiological substance, and configured for transmitting a corresponding detection signal to the evaluation unit (110).

The monitoring system (150) of the preceding embodiment, comprising a support body (132) to be located outside of the physiological subject (106) and accommodating the electromagnetic radiation source (124) and the electromagnetic radiation detector (128).

The monitoring system (150) of any of the eight preceding embodiments, including an insertion needle (132) configured to be selectively insertable into the catheter (108) for inserting the catheter (108) into the physiological subject (106) or retractable out of the catheter (108) after the insertion of the catheter (108) into the physiological subject (106).

The monitoring system (150) of any of the eight embodiments prior to the preceding embodiment, including a hollow insertion needle (132) configured so that the catheter (108) is selectively insertable into the insertion needle (132) for inserting the catheter (108) into the physiological subject (106) and that the insertion needle (132) is retractable relative to the catheter (108) after the insertion of the catheter (108) into the physiological subject (106).

The monitoring system (150) of any of the ten preceding embodiments, wherein the substrate (104) of the sensor arrangement (100) is formed as part of the catheter (108).

A method of detecting a physiological substance in a body material (102) of a physiological subject (106), the method including triggering an interaction between a sensor arrangement (100) and the body material (102) comprising the physiological substance, wherein the sensor arrangement (100) has a substrate (104) connected with a first sensor structure (202) configured for sensing the physiological substance electrochemically and connected with a second sensor structure (204) configured for sensing the physiological substance by a luminescence detection; detecting a first sensor signal indicative of the physiological substance based on an electrochemical response of the first sensor structure (202) upon interaction with the physiological substance; detecting a second sensor signal indicative of the physiological substance based on luminescence properties of the second sensor structure (204) upon interaction with the physiological substance; evaluating the first sensor signal and the second sensor signal in common.

A method of manufacturing a sensor arrangement (100) for detecting information indicative of a physiological substance in a body material (102), the method including connecting, particularly integrally connecting, a first sensor structure (202) to a substrate (104) and configuring the first sensor structure (202) for sensing the physiological substance electrochemically; connecting, particularly integrally connecting, a second sensor structure (204) with the substrate (104) and configuring the second sensor structure (204) for sensing the physiological substance by a luminescence detection.

The invention claimed is:

1. A sensor arrangement for detecting information indicative of a physiological substance in a body material of a physiological subject, the sensor arrangement comprising:
   a substrate;
   a first sensor structure connected to the substrate and being configured for sensing the physiological substance electrochemically; and
   a second sensor structure connected to the substrate and being configured for sensing the physiological substance by a luminescence detection,
   wherein the first sensor structure comprises an electrode and an enzyme comprising structure, the electrode being configured for electrically detecting a product of an enzyme-catalyzed chemical reaction between the physiological substance and an educt,
   wherein the second sensor structure comprises a luminescent substance having luminescent properties which change upon change of an amount of the educt of the enzyme-catalyzed chemical reaction, and
   wherein the electrode is arranged directly on the substrate, the luminescent substance is arranged in a surface portion of the sensor arrangement and is configured to contact the body material, and the enzyme comprising structure is arranged between the electrode and the luminescent substance.

2. The sensor arrangement of claim 1, wherein at least one of the first sensor structure and the second sensor structure is configured as at least one layer formed in and/or on and/or above the substrate, and wherein the first sensor structure and the second sensor structure together constitute a layer sequence on the substrate.

3. The sensor arrangement of claim 1, wherein the second sensor structure comprises a permeable membrane in which the luminescent substance is embedded.

4. The sensor arrangement of claim 1, wherein at least a part of the first sensor structure and at least a part of the second sensor structure are integrated into a common physical body so that a sensor event detectable by the first sensor structure and a sensor event detectable by the second sensor structure both occur within the common physical body.

5. The sensor arrangement of claim 1, wherein the second sensor structure is formed directly on the first sensor structure and the first sensor structure is formed directly on the substrate to thereby space the substrate with regard to the second sensor structure.

6. The sensor arrangement of claim 1, wherein both the first sensor structure and the second sensor structure are configured for detecting glucose as the physiological substance.

7. A monitoring system for monitoring a physiological substance in a body material of a physiological subject, the monitoring system comprising:
   a catheter being implantable in the physiological subject;
   a sensor arrangement integrated with the catheter, the sensor arrangement having a substrate, a first sensor structure connected to the substrate and a second sensor structure connected to the substrate, the sensor arrangement arranged such that the first sensor structure and the second sensor structure interact with a body material comprising the physiological substance in the physiological subject when the catheter is implanted in the physiological subject, the first sensor structure having an electrode and a structure comprising an enzyme, the electrode configured to electrochemically detect a product of an enzyme-catalyzed chemical reaction between the physiological substance and an educt, the second sensor structure having a luminescent substance having properties that change upon change of an amount of the educt of the enzyme-catalyzed chemical reaction, the second sensor configured to sense the physiological substance by a luminescence detection, wherein the electrode is arranged directly on the substrate, the luminescent substance is arranged in a surface portion of the sensor arrangement and is configured to contact the body material, and the enzyme comprising structure is arranged between the electrode and the luminescent substance; and
   an evaluation unit configured for evaluating a first sensor signal and a second sensor signal of the sensor arrangement in common, wherein the first sensor signal is detected as an electrochemical response of the first sensor structure upon interaction of the physiological substance with the first sensor structure, and the second sensor signal is detected as a response of luminescence properties of the second sensor structure upon interaction with the physiological substance.

8. The monitoring system of claim 7, wherein the catheter is a catheter tube, and wherein the sensor arrangement is arranged circumferentially at the catheter tube.

9. The monitoring system of claim 7, further comprising:
   a supply unit configured for supplying a physiologically active substance to the physiological subject in a quantity depending on a result of the evaluation of the evaluation unit.

10. The monitoring system of claim 9, wherein the supply unit is configured for supplying the physiologically active substance to the physiological subject via a permeable section of the catheter.

11. The monitoring system of claim 7, further comprising:
   an electrically conductive signal supply structure configured for transmitting an electric stimulus signal to the first sensor structure; and
   an electrically conductive detection structure configured for transmitting an electric detection signal to the evaluation unit, the electric detection signal being generated at the first sensor structure in response to the electric stimulus signal upon interaction of the sensor arrangement with the physiological substance.

12. The monitoring system of claim 7, further comprising:
   an electromagnetic radiation source configured for transmitting primary electromagnetic radiation to the second sensor structure; and an electromagnetic radiation detector configured for detecting secondary electromagnetic radiation generated at the second sensor structure in response to the primary electromagnetic radiation upon interaction of the sensor arrangement with the physiological substance, and configured for transmitting a corresponding detection signal to the evaluation unit.

13. The monitoring system of claim 7, further comprising:
an insertion needle configured to be selectively insertable into the catheter for inserting the catheter into the physiological subject or retractable out of the catheter after the insertion of the catheter into the physiological subject.

14. The monitoring system of claim 7, further comprising:
a hollow insertion needle configured so that the catheter is selectively insertable into the insertion needle for inserting the catheter into the physiological subject and that the insertion needle is retractable relative to the catheter after the insertion of the catheter into the physiological subject.

15. A method of manufacturing a sensor arrangement for detecting information indicative of a physiological substance in a body material, the method comprising:
connecting a first sensor structure to a substrate and configuring the first sensor structure for sensing the physiological substance electrochemically; and
connecting a second sensor structure with the substrate and configuring the second sensor structure for sensing the physiological substance by a luminescence detection,
wherein the first sensor structure is arranged with an electrode and a structure comprising an enzyme, the electrode configured to electrochemically detect a product of an enzyme-catalyzed chemical reaction between the physiological substance and an educt, the second sensor structure having a luminescent substance with properties that change upon change of an amount of the educt of the enzyme-catalyzed chemical reaction, the second sensor structure configured to sense the physiological substance by a luminescence detection, and
wherein the electrode is arranged directly on the substrate, the luminescent substance is arranged in a surface portion of the sensor arrangement and is configured to contact the body material, and the enzyme comprising structure is arranged between the electrode and the luminescent substance.

16. The method of claim 15, wherein the first sensor structure comprises an enzyme layer and an electrode, and wherein the electrode is deposited on the substrate.

* * * * *